United States Patent [19]

Bonzel

[11] Patent Number: 5,002,531
[45] Date of Patent: Mar. 26, 1991

[54] DILATION CATHETER WITH AN INFLATABLE BALLOON

[76] Inventor: Tassilo Bonzel, Neumattenstrasse 27, D-7800 Freiburg, Fed. Rep. of Germany

[21] Appl. No.: 290,107
[22] PCT Filed: Jun. 6, 1987
[86] PCT No.: PCT/DE87/00264
  § 371 Date: Dec. 5, 1988
  § 102(e) Date: Dec. 5, 1988
[87] PCT Pub. No.: WO88/00071
  PCT Pub. Date: Jan. 14, 1988

[30] Foreign Application Priority Data
  Jun. 26, 1986 [DE] Fed. Rep. of Germany ....... 3621350

[51] Int. Cl.[5] ............................................ A61M 25/10
[52] U.S. Cl. .................................... 604/96; 606/194
[58] Field of Search .................................. 604/96–103, 604/281, 282; 606/192, 194; 128/207.15

[56] References Cited

U.S. PATENT DOCUMENTS

| 3,731,692 | 5/1973 | Goodyear | 604/100 |
| 3,833,004 | 9/1974 | Vazquez | 604/100 |
| 4,141,364 | 2/1979 | Schultze | . |
| 4,183,102 | 1/1980 | Guiset | 604/101 |
| 4,198,981 | 4/1980 | Sinnreich | 604/101 |
| 4,403,612 | 9/1983 | Fogarty | 604/101 |
| 4,585,000 | 4/1986 | Hershenson | 606/194 |
| 4,762,129 | 8/1988 | Bonzel | 604/96 |

FOREIGN PATENT DOCUMENTS

| 0130805 | 6/1932 | Fed. Rep. of Germany | 604/102 |
| 3442736 A1 | 11/1984 | Fed. Rep. of Germany | . |
| 3621350 C2 | 6/1986 | Fed. Rep. of Germany | . |
| 2077111A | 6/1980 | United Kingdom | . |

Primary Examiner—C. Fred Rosenbaum
Assistant Examiner—William W. Lewis
Attorney, Agent, or Firm—Jeffers, Hoffman & Niewyk

[57] ABSTRACT

A dilation catheter is provided with an inflatable balloon which can be made to advance into a narrowed coronary artery along a guide wire placed by a guide catheter. An inflating tubular body is provided for expanding the balloon, which consists of a hose-like outer skin to which is connected, at the axially oriented edges, an inner skin also having a hose-like shape. Between the inner skin and the outer skin is a balloon interior space which surrounds an open central lumen extending axially through the balloon and ensures during dilatation a constant flow of blood into the coronary artery.

16 Claims, 1 Drawing Sheet

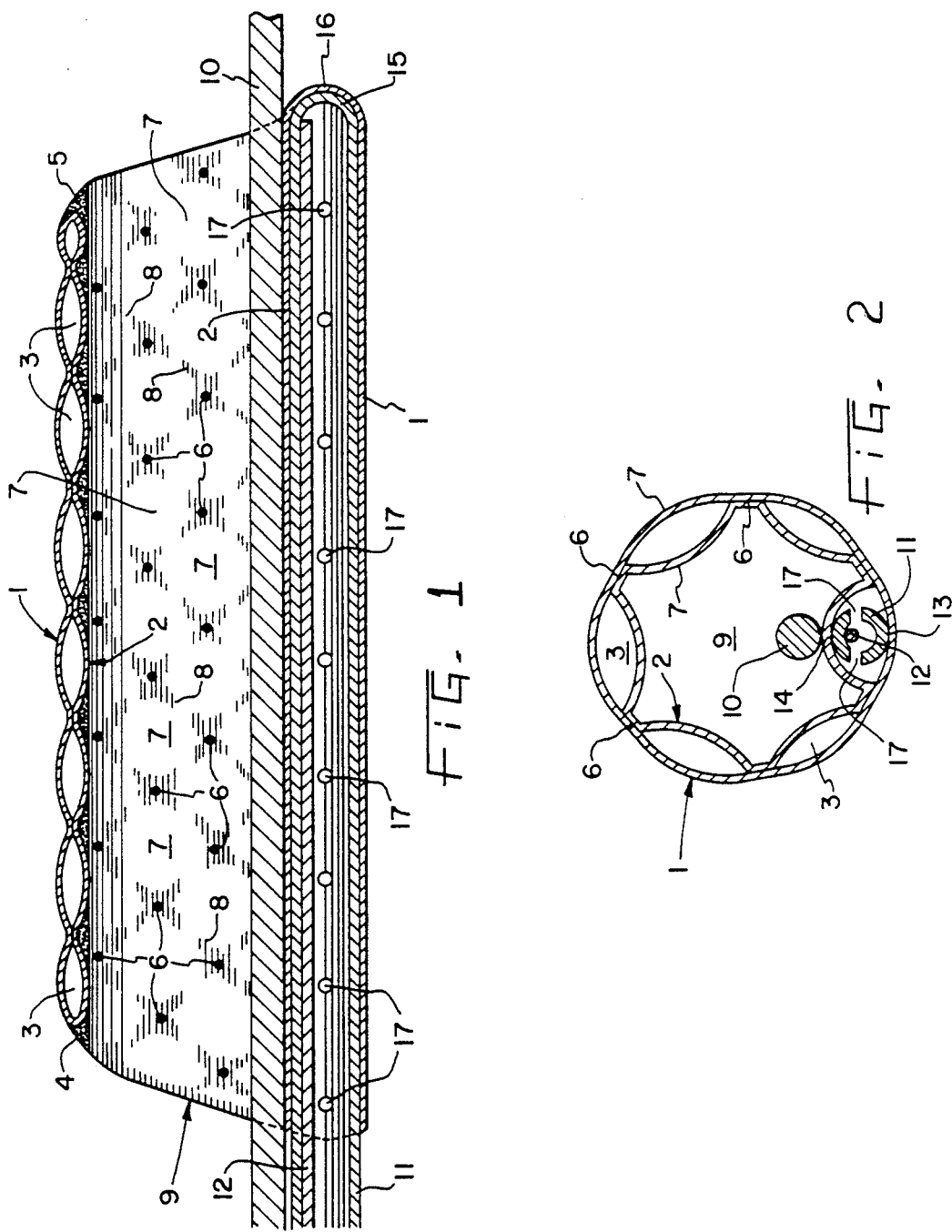

DILATION CATHETER WITH AN INFLATABLE BALLOON

The invention concerns a dilation catheter with an inflatable balloon which along a guide wire can be advanced into a constricted coronary artery and is connected with an inflating, tubular body through which a medium can be forced into the interior of the balloon for inflating it.

Such a dilation catheter is previously known from the German patent disclosure 34 42 736 and serves specifically the widening of constrictions in coronary arteries. For that purpose, a guide catheter with a wide interior lumen is advanced from the groin or the angle of the elbow of a patient through the large body arteries up to shortly before the exit of the coronary arteries in the aortic arch, with a radiological presentation of the coronary artery and the constriction being made under x-ray with intermittent administration of a contrast agent through the guide catheter. For guidance of the dilation catheter to be inserted, a fine guide wire with a soft point is advanced through the guide catheter into the coronary artery beyond the constriction. A control of the guide wire is possible through rotation, with a variably bent point.

The dilation catheter is in a next step advanced from outside, by way of a guide wire which serves as a guide rail, and through the guide catheter until the balloon of the dilation catheter lies in the constriction. The dilation then takes place through a one-time or repeated inflation of the balloon at a pressure of about 500 to 1200 kPa. Clinical experience has shown that longer dilation times are more favorable than shorter dilation times for stabilization of the expanded arterial constriction. During dilation, however, the flow of blood is interrupted in the artery when using the known dilation catheter, which interruption of the blood flow in the hard muscle should not exceed 30 to 120 seconds.

As the constriction in the coronary artery is widened under the pressure of the balloon, the laminar structure of the arterial wall might be damaged, leading to complications. These consist in an occlusion of the artery after dilation, by separation and prolapse of the inner wall layers and, in rare cases, a wall rupture with bleeding. If one of the above complications with arterial occlusion occurs after dilation and removal of the balloon, such results in individual cases in an immediate surgical intervention and an increased risk for the patient. Therefore, dilations of larger coronary arteries are performed under acute surgical readiness, whereby the organizational expense and the cost of an operation using a dilation catheter are increased considerably.

Another disadvantage of the prior dilation catheters is that during the dilation process the blood supply in the artery is interrupted, which leads to an insufficient perfusion of the adjacent tissue. Basing on this prior art, the problem underlying the invention is to provide a dilation catheter which makes it possible to assure during dilation and in the case of a complication a sufficient and continuous blood flow for a sufficient period of time so as to enable a prolongation of the dilation time.

This problem is inventionally solved in that the balloon features a tubular outer skin and, connected with it at least on the edges pointing in the axial direction, a tubular inner balloon skin between which a cross-sectionally essentially annular balloon interior is formed which is connected with the inflating tubular body and which surrounds a central lumen which in axial direction is open on both ends.

Due to the fact that the balloon interior forms an arrangement of annular swell bodies with a central lumen, the blood flow in the artery is not interrupted during dilation when using the inventional dilation catheter, so that the dilation time can be considerably prolonged. In this way it is possible to achieve a better stabilization of the wall and, in the case of a complication, prolong the period of time up to the surgical intervention, or even omit a surgical intervention, after stabilization of the arterial wall.

In a suitable embodiment of the invention, the balloon outer skin and the balloon inner skin are connected with each other at a number of points after quilting style so as to form a number of cushion type swell bodies which upon injection of a gas or liquid impart to the tubular or hose type dilation catheter, which is provided with a central lumen, a sufficiently high rigidity and dilatory force.

Suitable embodiments and developments of the invention are characterized in the subclaims.

An embodiment of the invention will be more fully explained hereafter with the aid of an embodiment illustrated in the drawing.

FIG. 1 shows an inventional dilation catheter in longitudinal section and

FIG. 2, an inventional dilation catheter in cross section.

The dual wall dilation catheter illustrated in FIG. 1 in longitudinal section and in FIG. 2 in cross section features a balloon outer skin 1 which is made, depending on requirement, of an elastic or nonelastic material and forms essentially an outer hose for the dual wall dilation catheter. Provided approximately concentrically with the balloon outer skin 1 is a balloon inner skin 2 which consists, depending on requirement, of an elastic or nonelastic material. The balloon inner skin 2 is as well essentially tubular, with a balloon interior space 3 forming between the balloon outer skin 1 and the balloon inner skin 2, which interior space may be fashioned, e.g., as an annular gap between the balloon outer skin 1 and the balloon inner skin 2. The balloon outer skin 1 and the balloon inner skin 2 are glued or welded to one another on their axial edges 4, 5 so that the balloon interior space 3 is sealed in axial direction.

The tubular or hose type balloon which in this way is formed through the balloon outer skin 1 of larger diameter and the balloon inner skin 2 with a smaller diameter may be fixed and stabilized in its structure, for instance by several glue connections or weld connections, between the balloon outer skin 1 and the balloon inner skin 2, which extend in axial and/or radial direction.

In the embodiment illustrated in FIGS. 1 and 2, the tubular balloon formed by the balloon outer skin 1 and the balloon inner skin 2 is structured in quilt fashion by a number of spot connections 6. At the spot connections 6 between the balloon outer skin 1 and the balloon inner skin 2, these may be glued or welded to one another. Created in this fashion are swell bodies in the form of cushion-shaped partitions 7 of the balloon interior space 3, with the individual cushion-shaped partitions 7 connecting with each other by way of unconnected areas 8, so that a liquid or gas used for widening the dual wall dilation catheter can communicate between the cushion-shaped partitions 7 of the balloon interior space 3, that is, can advance through the unconnected areas 8 into all cushion-shaped partitions 7 of the balloon interior 3. Therefore, the side of the ring-shaped balloon of the dilation catheter that points outside and the side of the balloon that points inside are in dilated condition fashioned, in their surface structure, similar to a quilt. Due to the internal pressure in the balloon interior 3, which in stationary condition is identical in all cushion-shaped partitions 7, the balloon forms with its outer skin 1 and its inner skin 2 a tubular structure or the structure of a dual wall tube. Obtained thereby is a mechanical stability and a specific natural stability although the balloon inner skin 2 leaves a central lumen 9 open which in the axial direction extends through the dilation catheter and permits in the inflated condition of the dilation catheter a blood circulation through the dilated artery.

As can be seen from FIGS. 1 and 2, extending through the central lumen 9 is a guide wire 10 that serves as a slide rail or guide rail and along which the balloon of the dilation catheter can be advanced through a usual hose type guide catheter up to the location of the desired intervention in the coronary artery. During the advance, the balloon interior 3 is preferably not filled yet with an inflating medium, so that the radial dimension of the balloon of the dilation catheter and of the central lumen 9 are smaller until the location of the intervention is reached, than illustrated in FIGS. 1 and 2.

As is evident from FIGS. 1 and 2, an inflating tubular body 11 protrudes eccentrically into the balloon space 3 of the dilation catheter. The inflating tubular body 11 is reinforced and, within the guide catheter illustrated in the drawing, transmits in axial direction the forces required for the advance and retraction of the balloon. For reinforcement and for increasing the buckle resistance, a stabilizing wire 12 may be provided inside the inflating tubular body 11, which wire is illustrated in FIGS. 1 and 2.

The inflating tubular body extends preferably in an axial direction, starting on one end 5 up to the opposite end 4 of the balloon interior skin 2 and the balloon outer skin 1 and from there across the required length for connection of the inflating medium. Provided on both sides beside the inflating tubular body 11, axially spaced, are several spot connections 6 that are aligned on one another and which fix the position of the inflating tubular body 11, in the way evident from FIG. 2, in the tubular space between the balloon outer skin 1 and the balloon inner skin 2. Besides, the inflating tubular body 11 can be glued or welded to the balloon outer skin 1 and the balloon inner skin 2 along the contact lines 13, 14.

On the left side in FIG. 1, the inflating tubular body 11 is connected, in a way not illustrated in detail in FIG. 1, in the peripheral direction along its outside surface with the dilation catheter so as to seal the balloon interior 3 outwardly. On the right-hand side in FIG. 1, the inflating tubular body 11 is sealed on its front end 15. Provided along the front end 15 is a connecting bead 16 through which the balloon outer skin 1 and the balloon inner skin 2 are connected with each other for sealing the balloon interior 3.

From FIGS. 1 and 2 it can be seen that the inflating tubular body 11 communicates through a number of openings 17 with the balloon interior 3, so that an inflating medium forced into the inflating tubular body 11 can proceed into the cushion-shaped partitions 7 so as to inflate in this way the tubular balloon, which in empty condition is folded together, and cause it to become stiff.

When the balloon inner skin 2 consists of elastic material and the balloon outer skin 1 of a nonelastic material, this causes the outside diameter of the balloon of the dilation catheter to be essentially independent of the inflating medium pressure. The balloon outer skin 1 acts thereby as a holding membrane. The elastic balloon inner skin 2 could be very small in uninflated condition (small surface) and cause a considerable reduction in diameter, through elastic restoration forces, as the balloon is deflated. This results in an especially easy passage of the dilation catheter as it is advanced or retracted through the guide catheter and/or the respective artery.

When instead of the balloon inner skin 2 only the balloon outer skin 1 is made of an elastic material, the balloon width can be varied in contingence on the pressure of the inflating medium, with the cross-sectional area of the central lumen 9 remaining essentially constant in the inflated balloon. When both the balloon outer skin 1 and the balloon inner skin 2 are made from elastic material, an increase of the inflating medium pressure causes predominantly an expansion of the outer membrane, i.e., of the balloon outer skin 1.

Due to the especially small volume of the balloon interior 3, quickly resorbable gases such as $CO_2$ and $N_2O$ can be used instead of liquids. While air quantities of, e.g., $1/10$ mm$^3$ can lead to damage when the balloon dilation catheter bursts, small quantities of $N_2O$ or $CO_2$ of less than $1/10$ mm$^3$ are quickly resorbed and hardly result in damage. This makes it possible to keep the lumen in the inflating tubular body 11 extremely small. If such is desired, the structure of the dilation catheter as discussed above makes it possible to exert only a slight pressure effect on the surrounding tissue. Thereof follows that the use of a dilation catheter with a dual wall ring-shaped balloon is especially suitable whenever higher pressures are not required. This is the case with unsclerosed arterial constrictions and in the case of stenoses which have already been dilated with the aid of a conventional balloon catheter, and at that, especially when complications have occurred with the use of a usual balloon catheter which does not feature a central lumen. In such a case it is possible to quickly substitute the dilation catheter described above for the previously used single-wall balloon catheter so as to avoid complications or, when complications already have occurred, achieve a stabilization durably or until surgical intervention.

I claim:

1. A dilation catheter that is advanceable into a constricted coronary artery, said catheter comprising:
    an inflating tubular body;
    an inflatable balloon adapted to move along a guide wire and including an elongate balloon outer skin and an elongate balloon inner skin, each said elongate balloon skin having opposed axial ends;
    said outer skin and said inner skin being connected to one another at their axial ends and at a plurality of points intermediate said axial ends in quilt fashion and along several interrupted lines which extend in an axial direction of the catheter; and
    a balloon interior space defined by said inner skin and said outer skin and having an essentially annular cross section, said balloon interior space being connectable to said inflating tubular body through which a fluid medium may be forced into said balloon interior space for inflation of said balloon;

said balloon interior space surrounding an axially extending central elongated lumen, which is open at both axial ends.

2. Dilation catheter according to claim 1, characterized in that the guide wire (10) extends through the central lumen (9) in the balloon.

3. Dilation catheter according to claim 1, characterized in that the inflating tubular body (11) is stiffened by a stabilization member (12). Which therefor extends in longitudinal direction.

4. Dilation catheter according to claim 3, characterized in that the stabilization is realized by a stabilizing wire (12).

5. Dilation catheter according to claim 1, characterized in that the inflating tubular body (11) traverses the balloon interior (3) in an axial direction and includes an opening (17) which empties into the balloon interior (3).

6. Dilation catheter according to claim 1, characterized in that the inflating tubular body (11) is outwardly sealed at the entrance point into the balloon interior (3).

7. Dilation catheter according to claim 1, characterized in that the balloon outer skin (1) and the balloon inner skin (2) consist of nonelastic material.

8. Dilation catheter according to claim 1, characterized in that the balloon outer skin (1) and the balloon inner skin (2) consist of elastic material.

9. Dilation catheter according to claim 1, characterized in that the balloon outer skin (1) consists of an elastic material and the balloon inner skin (2) of a nonelastic material.

10. Dilation catheter according to claim 1, characterized in that the balloon outer skin (1) consists of an nonelastic and the balloon inner skin (2) of an elastic material.

11. Dilation catheter according to claim 1, wherein said balloon includes a free wall and a fixed wall, said free wall being opposite said inflating tubular body and said fixed wall connected with said inflating tubular body, wherein said axial ends extend diagonal to the longitudinal axis of said inflating tubular body, with the axial length of balloon skin being smaller on said free wall than it is on said fixed wall.

12. A dilation catheter that is advanceable into a constricted coronary artery, said catheter comprising:
an inflating tubular body;
an inflatable balloon adapted to move along a guide wire and including an elongate balloon outer skin and an elongate balloon inner skin, each said elongate balloon skin having opposed axial ends;
said outer skin and said inner skin being connected to one another at their axial ends and at a plurality of points intermediate said axial ends in quilt fashion and along several interrupted lines which extend in an axial direction of the catheter; and
a balloon interior space defined by said inner skin and said outer skin and having an essentially annular cross section, said balloon interior space being connectable to said inflating tubular body through which a fluid medium may be forced into said balloon interior space for inflation of said balloon;
said balloon inter space surrounding an axially extending central elongated lumen, which is open at both axial ends;
the guide wire extending through said central lumen;
said inflating tubular body being stiffened by a stabilization wire which extends along the axial length of the catheter.

13. A dilation catheter according to claim 12 characterized in that the inflating tubular body traverses the balloon interior space in an axial direction and includes an opening which connects the interior of said inflating tubular body with the balloon interior space.

14. A dilation catheter according to claim 12 characterized in that the inflating tubular body is outwardly sealed at the entrance point into the balloon interior.

15. A dilation catheter that is advanceable into a constricted coronary artery, said catheter comprising:
an inflating tubular body;
an inflatable balloon adapted to move along a guide wire and including an elongate balloon outer skin and an elongate balloon inner skin, each said elongate balloon skin having opposed axial ends;
said outer skin and said inner skin being connected to one another at their axial ends and at a plurality of points intermediate said axial ends in quilt fashion and along several interrupted lines which extend in an axial direction of the catheter;
said outer skin and said inner skin being further connected to one another at their axial edges; and
a balloon interior space defined by said inner skin and said outer skin and having an essentially annular cross section, said balloon interior space being connectable to said inflating tubular body through which a fluid medium may be forced into said balloon interior space for inflation of said balloon;
said balloon interior space surrounding an axially extending central elongated lumen, which is open at both axial ends;
said inflating tubular body being outwardly sealed at the entrance point into said balloon interior space.

16. Dilation catheter according to claim 15, wherein said balloon includes a free wall and a fixed wall, said free wall being opposite said inflating tubular body and said fixed wall connected with said inflating tubular body, wherein said axial ends extend diagonal to the longitudinal axis of said inflating tubular body, with the axial length of balloon skin being smaller on said free wall than it is on said fixed wall.

* * * * *